(12) United States Patent
Capener (10) Patent No.: US 8,537,174 B2
(45) Date of Patent: Sep. 17, 2013

(54) TECHNIQUES FOR ADAPTIVE BRIGHTNESS CONTROL OF A DISPLAY

(75) Inventor: Christopher L Capener, Cupertino, CA (US)

(73) Assignee: Palm, Inc., Sunnyvale, CA (US)

( * ) Notice: Subject to any disclaimer, the term of this patent is extended or adjusted under 35 U.S.C. 154(b) by 864 days.

(21) Appl. No.: 12/574,540

(22) Filed: Oct. 6, 2009

(65) Prior Publication Data

US 2011/0080421 A1 Apr. 7, 2011

(51) Int. Cl.
*G09G 5/02* (2006.01)
*G09G 5/10* (2006.01)

(52) U.S. Cl.
USPC .......................................... 345/589; 345/690

(58) Field of Classification Search
None
See application file for complete search history.

(56) References Cited

U.S. PATENT DOCUMENTS 5,422,544 A * 6/1995 Giddings et al. .............. 315/156
7,744,216 B1 * 6/2010 Uhlhorn ........................ 351/204

OTHER PUBLICATIONS

IBM; Automatically Correct Monitor/Screen Brightness Based on Users Pupils or Room Lighting; IP.com Prior Art Database; Nov. 7, 2006.*
"The Reaction of the Eye to Light," Prentice Reeves Research Laboratory, Transactions of Optical Society, Oct. 1920.

* cited by examiner

*Primary Examiner* — Carlos Perromat (57) ABSTRACT

Techniques for adaptive brightness control of a display are described. A apparatus may comprise a display and a display control module communicatively coupled to the display. The display control module may be arranged to modify brightness levels for the display based on ambient light level measurements and changes in pupil size of a human eye. Other embodiments are described and claimed.

12 Claims, 6 Drawing Sheets

- MEASURE AMBIENT LIGHT LEVELS FOR A MOBILE COMPUTING DEVICE
  610

- MODIFY BRIGHTNESS LEVELS FOR A DISPLAY OF THE MOBILE COMPUTING DEVICE BASED ON THE AMBIENT LIGHT LEVEL MEASUREMENTS AND CHANGES IN PUPIL SIZE OF A HUMAN EYE
  620

*FIG. 6*

TECHNIQUES FOR ADAPTIVE BRIGHTNESS CONTROL OF A DISPLAY

BACKGROUND

A mobile computing device such as a combination handheld computer and mobile telephone or smart phone generally may provide voice and data communication functionality as well as computing and processing capabilities. Mobile computing devices typically include some form of electronic display with a backlight designed to emit light and therefore offer varying levels of brightness. In many cases, brightness levels for the display may be modified based on different ambient light situations to provide a more comfortable viewing experience. For instance, ambient light levels may be dynamic, changing over time or as the display is moved to a different location. Variations in ambient light affect a perceived brightness of the electronic display, causing the display to look too dim in a bright area and too bright in a dark area. Brightness levels for a display of a mobile computing device may be increased or decreased to accommodate dynamic changes in ambient light conditions to provide a consistent level of brightness. Enhanced techniques to manage brightness levels for a display in response to changes in ambient light conditions may therefore provide an enhanced viewing experience. It is with respect to these and other advantages that the present improvements are made.

DETAILED DESCRIPTION

Various embodiments are generally directed to adaptive brightness control techniques for electronic displays of a mobile computing device, such as a smart phone. Some embodiments are particularly directed to automatically and continuously modifying brightness levels for an electronic display based on ambient light levels and changes in pupil size of a human eye.

To enhance viewing experience, various embodiments implement an adaptive brightness control technique that calculates new brightness levels and varies a timed ramp between brightness levels in accordance with changes in pupil size for a human eye. A pupil generally changes in size according to various intensities of ambient light. This phenomenon is referred to as the pupillary light reflex. The pupillary light reflex causes pupil size to increase as ambient light levels decrease to allow more light to enter the eye. Conversely, the pupillary light reflex causes pupil size to decrease as ambient light levels increase to allow less light to enter the eye to prevent aberrations of light rays and thus attain its expected acuity. The rate of change in pupil size differs depending on whether there is an increase or decrease in ambient light levels. In general, pupil size changes faster in response to increases in brightness than to decreases in brightness. Various adaptive brightness control techniques may utilize a novel conversion algorithm that generates target brightness levels and a timed ramp based on one or more pupil size response curves. In this manner, a mobile computing device may reduce eyestrain from glare and reflection and provide a more consistent viewing experience. Furthermore, a mobile computing device may improve power conservation by saving power for a battery in lower lighting areas, extending a useful life for an electronic display and its components (e.g., a backlight) by extending mean time between failure, and other advantages as well.

Various embodiments include physical or logical structures arranged to perform certain operations, functions or services. The structures may comprise physical structures, logical structures or a combination of both. The physical or logical structures are implemented using hardware elements, software elements, or a combination of both. Descriptions of embodiments with reference to particular hardware or software elements, however, are meant as examples and not limitations. Decisions to use hardware or software elements to actually practice an embodiment depends on a number of external factors, such as desired computational rate, power levels, heat tolerances, processing cycle budget, input data rates, output data rates, memory resources, data bus speeds, and other design or performance constraints. Furthermore, the physical or logical structures may have corresponding physical or logical connections to communicate information between the structures in the form of electronic signals or messages. The connections may comprise wired and/or wireless connections as appropriate for the information or particular structure. It is worthy to note that any reference to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Figure 1:
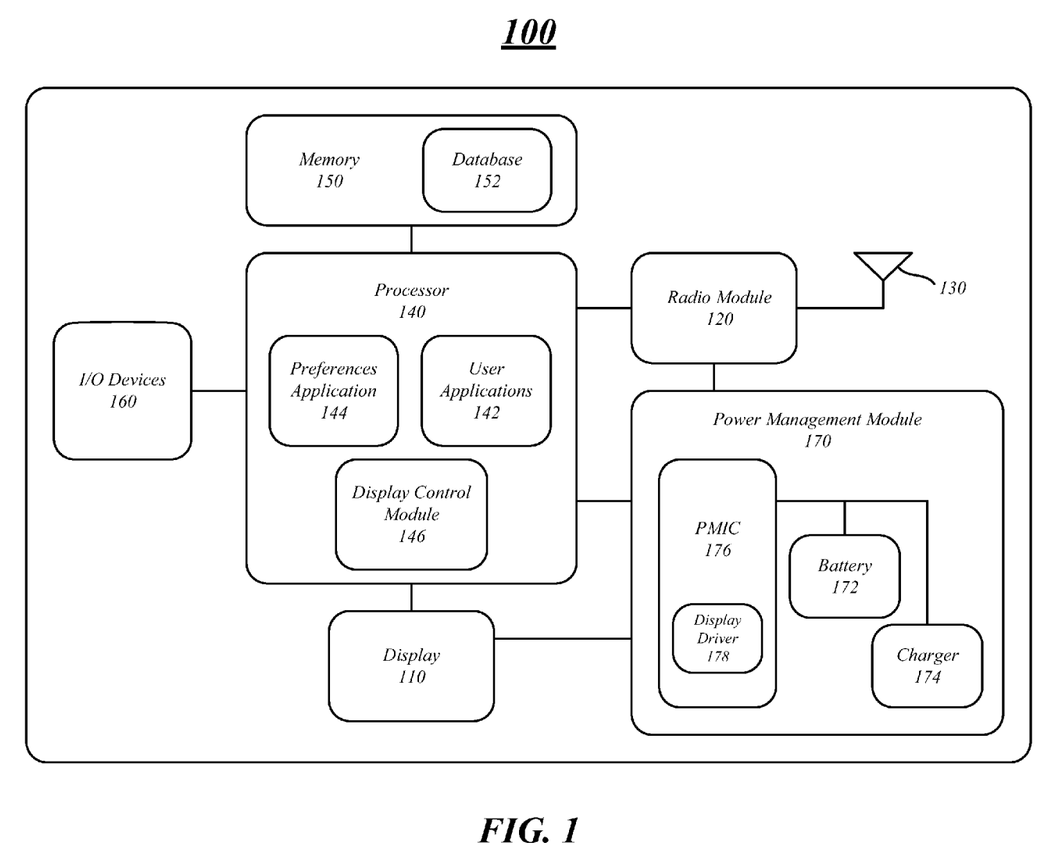
FIG. 1 illustrates one embodiment of a mobile computing device.

FIG. 1 illustrates a mobile computing device 100 suitable for implementing various embodiments. The mobile computing device 100 may comprise any electronic device having at least computing capabilities, mobility, and an electronic display. In some embodiments, the mobile computing device 100 may be implemented as a combination handheld computer and mobile telephone, sometimes referred to as a smart phone. Examples of smart phones include, for example, Palm® products such as Palm Pre™, Palm Pixi™, Palm Centro™, Palm Treo™, and other smart phones. Although some embodiments may be described with the mobile computing device 100 implemented as a smart phone by way of example, it may be appreciated that the mobile computing device 100 may be implemented as other types of a user equipment (UE), a mobile device, a mobile station, a mobile unit, a personal digital assistant (PDA), a mobile computing device, a smart phone, a cellular telephone, a handset, a one-way pager, a two-way pager, a messaging device, a computer, a personal computer (PC), a desktop computer, a laptop computer, a notebook computer, a netbook computer, a handheld computer, a tablet computer, a thin client, consumer electronics, a gaming device, or any other suitable electronic device having communications capabilities, computing capabilities and mobility.

In various embodiments, the mobile computing device 100 may be generally configured to support or provide cellular voice communication, wireless data communication, and various computing capabilities. In some embodiments, however, the mobile computing device 100 may be limited to only computing capabilities.

The mobile computing device 100 may support cellular voice communication with a mobile network such as a Code Division Multiple Access (CDMA) network, Global System for Mobile Communications (GSM) network, North American Digital Cellular (NADC) network, Time Division Multiple Access (TDMA) network, Extended-TDMA (E-TDMA) network, Narrowband Advanced Mobile Phone Service (NAMPS) network, third generation (3G) network such as a Wide-band CDMA (WCDMA) network, CDMA-2000 network, Universal Mobile Telephone System (UMTS) network, and others.

The mobile computing device 100 may support wireless wide area network (WWAN) data communication including Internet access. Examples of WWAN data communication services may include Evolution-Data Optimized or Evolution-Data only (EV-DO), Evolution For Data and Voice (EV-DV), CDMA/1xRTT, GSM with General Packet Radio Service systems (GSM/GPRS), Enhanced Data Rates for Global Evolution (EDGE), High Speed Downlink Packet Access (HSDPA), High Speed Uplink Packet Access (HSUPA), and others.

The mobile computing device 100 may support wireless local area network (WLAN) data communication in accordance with the Institute of Electrical and Electronics Engineers (IEEE) 802.xx series of protocols, such as the IEEE 802.11a/b/g/n series of standard protocols and variants (also referred to as "WiFi"), the IEEE 802.16 series of standard protocols and variants (also referred to as "WiMAX"), the IEEE 802.20 series of standard protocols and variants, and others.

The mobile computing device 100 also may support data communication in accordance with shorter range wireless networks, such as a wireless personal area network (PAN) offering Bluetooth® data communication services in accordance with the Bluetooth® Special Interest Group (SIG) series of protocols, specifications, profiles, and so forth. Other examples of shorter range wireless networks may employ infrared (IR) techniques or near-field communication techniques and protocols, such as electro-magnetic induction (EMI) techniques including passive or active radio-frequency identification (RFID) protocols and devices.

As shown in FIG. 1, the mobile computing device 100 may comprise, by way of example, an electronic display 110, a radio module 120, an antenna system 130, a processor 140, memory 150, input/output (I/O) devices 160, and a power management module 170. Although some embodiments may be illustrated and described as comprising exemplary functional components and/or modules performing various operations, it can be appreciated that such components or modules may be implemented in hardware, software, firmware, or in any combination thereof. In addition, while a limited number of functional components and/or modules may be shown for purposes of illustration, it can be appreciated that the mobile computing device 100 may include other elements in accordance with the described embodiments.

The display 110 may comprise any digital display device suitable for a mobile computing device and capable of emitting light at varying levels of brightness. For instance, the display 110 may be implemented by a liquid crystal display (LCD) such as a touch-sensitive, color, thin-film transistor (TFT) LCD, a plasma display, organic light emitting diode (OLED) displays, a cathode ray tube (CRT) display, or other type of suitable visual interface for displaying content to a user of the mobile computing device 100 and having some form of a backlight or brightness emitter.

The radio module 120 may comprise various radio elements, including a radio processor, one or more transceivers, amplifiers, filters, switches, and so forth. The radio module 120 may be arranged to provide voice and/or data communication functionality for the mobile computing device 100 for operating in accordance with different types of wireless network systems. It may be appreciated that the radio module 120 may utilize different radio elements to implement different communication techniques.

The antenna system 130 may comprise or be implemented as one or more internal antennas (e.g., antenna 104) and/or external antennas for transmitting and receiving electrical signals. In some embodiments, the antenna system 130 may support operation of the mobile computing device 100 in multiple frequency bands or sub-bands such as the 2.4 GHz range of the ISM frequency band for WiFi and Bluetooth® communications, one or more of the 850 MHz, 900 MHZ, 1800 MHz, and 1900 MHz frequency bands for GSM, CDMA, TDMA, NAMPS, cellular, and/or PCS communications, the 2100 MHz frequency band for CDMA2000/EV-DO and/or WCDMA/UMTS communications, the 1575 MHz frequency band for Global Positioning System (GPS) operations, and others.

The processor 140 may comprise a general purpose processor or an application specific processor arranged to provide general or specific computing capabilities for the mobile computing device 100. In some implementations, the mobile computing device 100 may comprise a dual processor architecture including the processor 140 and a radio processor implemented by the radio module 120 that communicate with each other using interfaces such as one or more universal serial bus (USB) interfaces, micro-USB interfaces, universal asynchronous receiver-transmitter (UART) interfaces, general purpose input/output (GPIO) interfaces, control/status lines, control/data lines, audio lines, and so forth. It may be appreciated that the mobile computing device 100 may use any suitable number of processors in accordance with the described embodiments.

In general, the processor 140 may perform operations associated with higher layer protocols and applications. Such applications generally may provide various user interfaces (UIs) to communicate information between the mobile computing device 100 and a user. Application programs may comprise upper layer programs running on top of the operating system (OS) of the processor 140 that operate in conjunction with the functions and protocols of lower layers including, for example, a transport layer such as a Transmission Control Protocol (TCP) layer, a network layer such as an Internet Protocol (IP) layer, and a link layer such as a Point-to-Point (PPP) layer used to translate and format data for communication.

The processor 140 may provide various user applications 142, such as messaging applications, web browsing applications, personal information management (PIM) applications (e.g., contacts, calendar, scheduling, tasks), Virtual Private Network (VPN) applications, word processing applications, spreadsheet applications, database applications, media applications (e.g., video player, audio player, multimedia player, digital camera, video camera, media management), location based services (LBS) applications, gaming applications, and so forth. Examples of messaging applications may include without limitation a cellular telephone application, a voice-mail application, a Voice-over-Internet Protocol (VoIP) application, a facsimile application, an e-mail application, a short message service (SMS) application, a multimedia message service (MMS) application, a video teleconferencing application, a push-to-talk (PTT) application, a push-to-video application, Text-to-Speech (TTS) application, an instant messaging (IM) application, and so forth. It is to be appreciated that the mobile computing device 100 may implement other types of applications in accordance with the described embodiments.

The processor 140 also may provide functional utilities that are available to various protocols, operations, and/or applications. Examples of such utilities include operating systems, device drivers, programming tools, utility programs, software libraries, application programming interfaces (APIs), and so forth. Exemplary operating systems may include, for example, a Palm webOS®, Palm OS®, Palm OS® Cobalt, Microsoft® Windows OS, Microsoft Windows® CE OS, Microsoft Pocket PC OS, Microsoft Mobile OS, Symbian OS™, Embedix OS, Linux OS, Binary Runtime Environment for Wireless (BREW) OS, JavaOS, a Wireless Application Protocol (WAP) OS, and so forth.

The memory 150 may comprise computer-readable storage media such as volatile or non-volatile memory units arranged to store programs and data for execution and/or use by the mobile computing device 100. For example, the memory 150 may store executable program instructions, code or data capable of being retrieved and executed by the processor 140 to provide operations for the mobile computing device 100. The memory 150 also may implement various databases and/or other types of data structures (e.g., arrays, files, tables, records) for storing data for use by the processor 140 and/or other elements of the mobile computing device 100.

The I/O devices 160 may comprise various devices for receiving input from and displaying content to a user of the mobile computing device 100 such as the display 110 (shown separately) for presenting UIs, various light emitting diodes (LEDs), and a keypad for inputting data, for example. The keypad may be implemented by an alphanumeric keypad having a QWERTY key layout and an integrated number dial pad. The keypad may comprise a physical keypad and/or a virtual keypad using soft buttons displayed on the display 110. The mobile computing device 100 may comprise various other I/O devices 160 including keys (e.g., input keys, preset and programmable hot keys), buttons (e.g., left and right action buttons, a multidirectional navigation button, phone/send and power/end buttons, preset and programmable shortcut buttons), switches (e.g., volume rocker switch, a ringer on/off switch having a vibrate mode), a microphone, speakers, an audio headset, a camera, a stylus, and so forth.

The power management module 170 may be arranged to supply and/or manage power for the mobile computing device 100, including the display 110, the radio module 120, the processor 140, and other elements of mobile computing device 100. For example, the power management module 170 may comprise a battery 172 (e.g., removable and rechargeable battery 103) for supplying direct current (DC) power as well as a charger 174 including an alternating current (AC) interface to draw power from an AC power source, such as a standard AC main power supply. In various implementations, the power management module 170 may comprise a power management integrated circuit (PMIC) 176 comprising circuitry and/or logic for distributing power from the battery 172 and/or charger 174 to the other elements of the mobile computing device 100. In such implementations, the PMIC 176 may supply power to one or more elements of the mobile computing device 100 via power I/O interfaces. In some cases, certain elements of the mobile computing device 100 may act as a power supply for other elements. For example, the processor 140 may comprise some I/O power interfaces for receiving power from the PMIC 176 and other I/O power interfaces for supplying power to elements of the mobile computing device 100 such as the display 110, the radio module 120, the memory 150, the I/O devices 160 (e.g., LED, keypad, camera, speakers, etc.), and others.

In various embodiments, the mobile computing device 100 may allow the user to set various global and/or application preferences for illuminating the display 110. As shown, the processor 140 may comprise a preferences application 144 for presenting one or more UIs for receiving input from the user of the mobile computing device 100. The user may view, input, and modify brightness preferences via the UIs using I/O devices 160 such as the display 110, keyboard, buttons, and so forth. After being input by the user, the brightness preferences may be stored in a database 152 within the memory 150 or other suitable computer-readable storage media.

In some implementations, the UIs for setting the brightness preferences may be accessible from the preferences application 144 as well from one or more user applications 142. For example, certain user applications 142 (e.g., messaging application, PIM application, media application, LBS application, gaming application, etc.) may include a menu item for allowing the user to associate one or more brightness effects with certain operations.

It can be appreciated that FIG. 1 depicts an exemplary implementation for purposes of illustration and that various configurations of hardware, software, and/or firmware may be employed to control the current and voltage supplied to the display 110 in accordance with the described embodiments. For example, in some embodiments, the display control module 146 may be implemented by or form part of one of the user applications 142 and/or the preferences application 144. In some embodiments, the display driver 178 may be implemented by the display 110, the processor 140, and/or a separate IC or microcontroller.

As previously described, the mobile computing device 100 includes the display 110 that is designed to display information for a viewer. To assist a viewer in reading displayed information, the display 110 may have a backlight mechanism arranged to emit light of varying levels of brightness or luminance. The amount of brightness may vary for any number of reasons. For instance, a viewer may use one or both of the applications 142, 144 to automatically manage brightness levels based on any number of user defined settings. For instance, a user may define a setting to control a length of time a backlight for the display 110 remains active whenever an I/O device 160 has not received any user input. This may be desirable to conserve power provided by the battery 172, for example. A viewer may also manually adjust brightness levels to accommodate different types of displayed information or ambient light conditions.

The mobile computing device 100 may control the display 110 using the display control module 146. The display control module 146 may generally control operations for the display 110. As the display 110 consumes a relatively large amount of power relative to other components of the mobile computing device 100, the display control module 146 is designed to coordinate with the power management module 170 in order to implement various power conservation techniques. Further, the display control module 146 may send control directives to the power management module 170 to increase or decrease power supplied to the display 110 to increase or decrease brightness levels for the display 110.

The display control module 146 may be arranged to automatically modify brightness levels for the display 110 based on ambient light level measurements. The display 110 includes a backlight designed to emit light and therefore offer varying levels of brightness. The display control module 146 automatically changes brightness levels for the display 110 based on different ambient light situations to provide a more comfortable viewing experience. For instance, ambient light levels may be dynamic, changing over time or as the display is moved to a different location. Variations in ambient light affect a perceived brightness of the display 110, causing the display 110 to look too dim or washed out in a bright area and too bright or intense in a dark area. The display control module 146 may increase or decrease brightness levels for the display 110 to accommodate dynamic changes in ambient light conditions to provide a consistent level of brightness for the display 110. By automatically managing brightness levels for the display 110 in response to changes in ambient light conditions, the display control module 146 and the mobile computing device 100 provides several advantages such as improving power conservation by saving power for the battery 172 in lower lighting areas, extending a useful life for the display 110 and its components (e.g., a backlight) by extending mean time between failure, providing an enhanced viewing experience for a user by reducing eyestrain from glare and reflection, and other advantages as well. The display control module 146 may be described in more detail with reference to FIG. 2.

Figure 2:
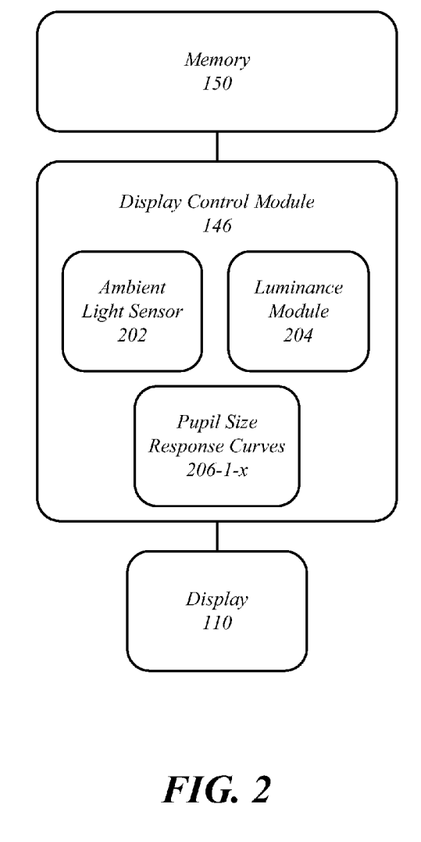
FIG. 2 illustrates one embodiment of a display control module.

FIG. 2 illustrates a more detailed block diagram for portions of the mobile computing device 100, particularly for the display control module 146. In the illustrated embodiment shown in FIG. 2, the display control module 146 comprises an ambient light sensor 202, a luminance module 204, and a timing module 206. The display control module 146 and its illustrated elements may be implemented using hardware, software, or a combination of hardware and software. Although the display control module 146 may be shown with a limited number of elements, it may be appreciated that more or less elements may be implemented for the display control module 146 as desired for a given implementation.

The display control module 146 may be generally arranged to automatically modify brightness levels for the display 110 based on ambient light levels around the mobile computing device 100. The display control module 146 may be particularly arranged to modify brightness levels for the display 110 based on ambient light level measurements and changes in pupil size of a human eye. By modifying brightness levels to accommodate changes in pupil size of a human eye as a reaction to changes in ambient light levels, a user may have a more comfortable viewing experience. For instance, the display control module 146 may gradually adjust brightness at a rate that matches a rate of change in pupil size of a user to provide a more consistent perceived brightness for the user of the display 110.

One or more ambient light sensors 202 may be used to measure ambient light levels around the mobile computing device 100. The one or more ambient light sensors 202 may measure ambient light levels for one or more defined fields proximate to the mobile computing device. Each ambient light sensor 202 may measure (or sample) ambient light levels on a continuous, periodic, aperiodic, continuous or on-demand basis. Any suitable ambient light sensor capable of detecting changes in visible light may be used, such as an array of PiN diodes implemented on a substrate, for example. The embodiments are not limited in this context.

Each ambient light sensor 202 may be positioned somewhere on the mobile computing device 100 to measure ambient light levels that might affect a user viewing content exposed on the display 110. In one embodiment, for example, a single ambient light sensor 202 may be placed on a front side of the mobile computing device 100 having the display 110. This allows the ambient light sensor 202 to measure ambient light levels from light sources behind a viewer, such as a sun or overhead light. In one embodiment, for example, a first ambient light sensor 202 may be placed on the front side and a second ambient light sensor 202 may be placed on a back side of the mobile computing device 100. This configuration may allow the first and second ambient light sensors 202 to measure ambient light levels from light sources behind a viewer and in front of a viewer. The latter configuration may be desirable, for example, when the mobile computing device 100 is operating in a camera mode using the display 110 as a viewfinder on the front side of the mobile computing device 100, and a camera lens on the back side of the mobile computing device 100. The exact number and placement of ambient light sensors 202 may be a design consideration and may vary for a given implementation.

The luminance module 204 may be generally arranged to convert ambient light level measurements to display brightness control values for the display 110 of the mobile computing device 100. For instance, the luminance module 204 may receive ambient light level measurements from the various ambient light sensors 202, combine them using a weighted average or other statistical average, convert the received ambient light level measurements to control directives in the form of display brightness control values, and output the display brightness control values to the power management module 170 and/or the display 110. The power management module 170 may then increase or decrease an amount of power provided to the display 110 by the battery 172 and/or the charger 174 via the PMIC 176 to cause a corresponding increase or decrease in brightness levels for the display 110 based on the brightness control values.

When a difference between a current brightness level and a target brightness level for the display 110 is above a defined threshold, a timed ramp may be used to move from the current brightness level to the target brightness level to allow a smoother transition for a viewer, thereby avoiding an abrupt change in brightness levels. The timed ramp is usually a linear ramp. More complex implementations may use a varying slope ramp that increases from zero at a beginning time to some maximum rate and then back to zero at an ending time. However, these approaches do not account for reaction of human eyes to changes in ambient light levels and/or brightness levels.

In various embodiments, display brightness control values may be derived using one or more aspects of a human eye, such as a rate of change in pupil size in response to ambient light. In one embodiment, for example, the luminance module 204 may convert ambient light level measurements to brightness control values using at least one pupil size response curve 206-1-$x$. The pupil size response curves 206-1-$x$ represent different changes in pupil size over time in response to changes in ambient light levels. The pupil size response curves 206-1-$x$ may be stored using a data structure such as a look-up table (LUT) in memory 150, with a LUT associating one or more ambient light level measurements with one or more pupil sizes. Additionally or alternatively, the pupil size response curves 206-1-$x$ may be dynamically computed using a mathematical formula. The embodiments are not limited in this context.

To enhance viewing experience the luminance module 204 may use a conversion algorithm that varies a timed ramp in accordance with changes in pupil size for a human eye. A pupil changes in size according to various intensities of ambient light. This phenomenon is referred to as the pupillary light reflex. The pupillary light reflex causes pupil size to increase as ambient light levels decrease to allow more light to enter the eye. Conversely, the pupillary light reflex causes pupil size to decrease as ambient light levels increase to allow less light to enter the eye to prevent aberrations of light rays and thus attain its expected acuity. The rate of change in pupil size differs depending on whether there is an increase or decrease in ambient light levels. In general, pupil size changes faster in response to increases in brightness than to decreases in brightness. The luminance module 204 may utilize a conversion algorithm that generates target brightness levels and a timed ramp based on one or more of the pupil size response curves 206-1-x.

In one embodiment, for example, the luminance module 204 may implement a conversion algorithm to determine a first target pupil size based on the ambient light level measurements received from the ambient light sensor 202, compare the target pupil size with a current pupil size, select a pupil size response curve 206-1-x based on the comparison, determine a second target pupil size from the selected pupil size response curve, and convert the second target pupil size to one or more display brightness control values for the display 110 using the selected pupil size response curve. The luminance module 204 may be further described using FIGS. 3-5.

Figure 3:
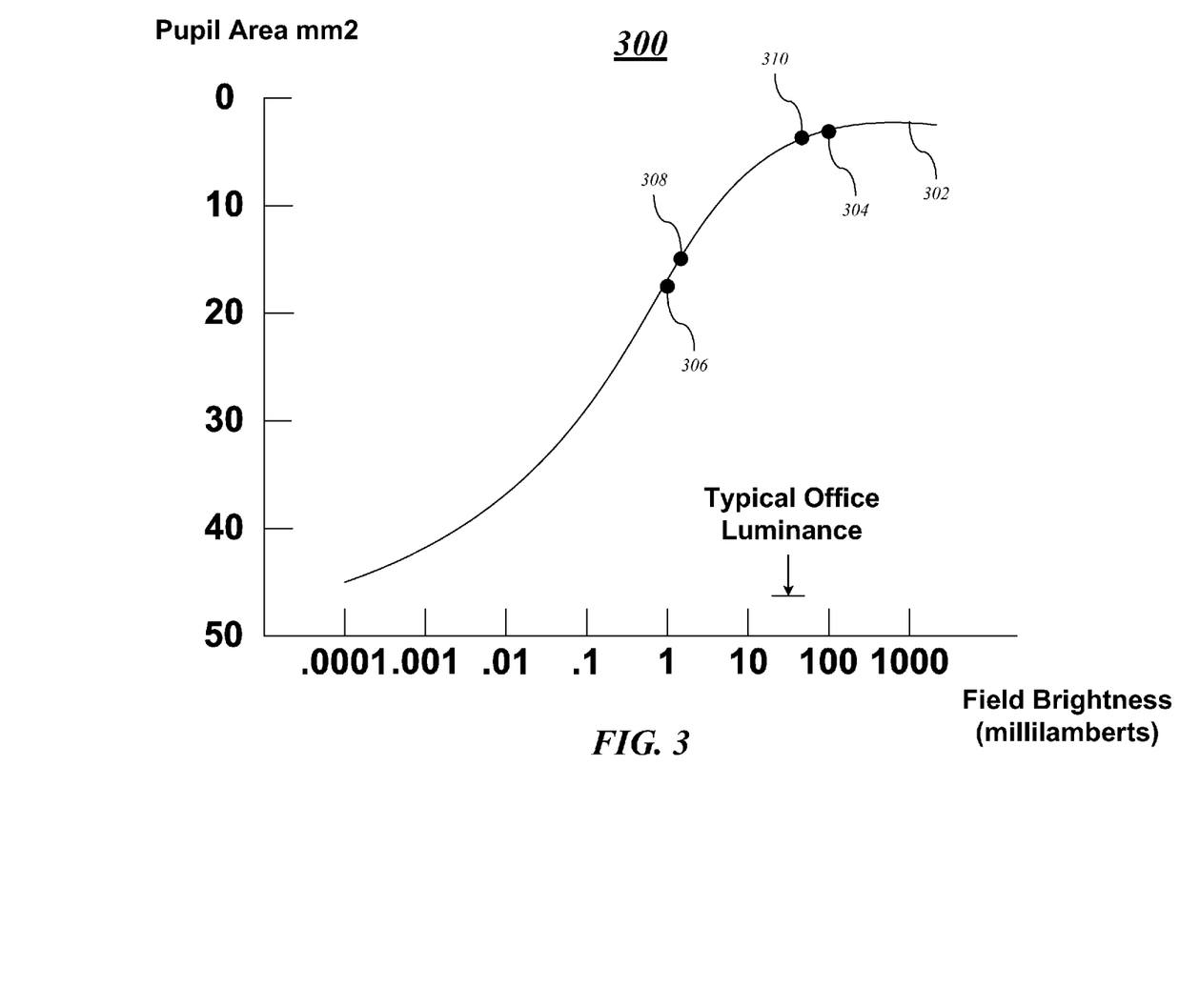
FIG. 3 illustrates an exemplary luminance graph.

FIG. 3 illustrates a luminance graph 300. The luminance graph 300 illustrates an example of a base pupil size response curve 302 illustrating pupil size as a function of a weighted average of luminance (or brightness) within a given field of view. The y-axis represents different pupil sizes (in mm$^2$) from 0 to 50. The x-axis represents different ambient light levels or field brightness in millilamberts (mL) from 0.0001 to 1000 mL, which can be converted to candela per square meter (cd/m$^2$) by multiplying mL by approximately 3.183. Typical ambient light levels are shown in Table 1 as follows:

TABLE 1

| Field Brightness (cd/m$^2$) | Pupil Diameter (mm) |
|---|---|
| 30 | Subdued indoor lighting |
| 60 | Less than typical office light, sometimes recommended for display only workplaces |
| 120 | Typical office |
| 240 | Bright indoor office |
| 480 | Very bright, precision indoor tasks |
| 960 | Usual outdoors |
| 1920 | Bright afternoon |

The luminance module 204 may begin computing display brightness control values for the display 110 by determining a target pupil size from the base pupil size response curve 302 based on the ambient light level measurements received from the ambient light sensor 202. For instance, when the mobile computing device 100 moves from an environment with a lower luminance value of 1 mL (darker room) to an environment with a higher luminance value of 100 mL (lighter room), the luminance module 204 may receive a weighted average of ambient light level measurements of approximately 100 mL from the ambient light sensor 202, and determine a target pupil size 304 of approximately 3 mm.

The luminance module 204 may compare a target pupil size with a current pupil size to select a pupil size response curve suitable for use in calculating display brightness control levels for the display 110. For example, assume a current pupil size 306 is approximately 17 mm since the mobile computing device 100 was in an environment with a lower luminance value of 1 mL prior to moving. The luminance module 204 compares the current pupil size 306 of 17 mm with the target pupil size 304 of 3 mm, and selects a second type of pupil size response curve 206-1-x based on the comparison results.

Figure 4:
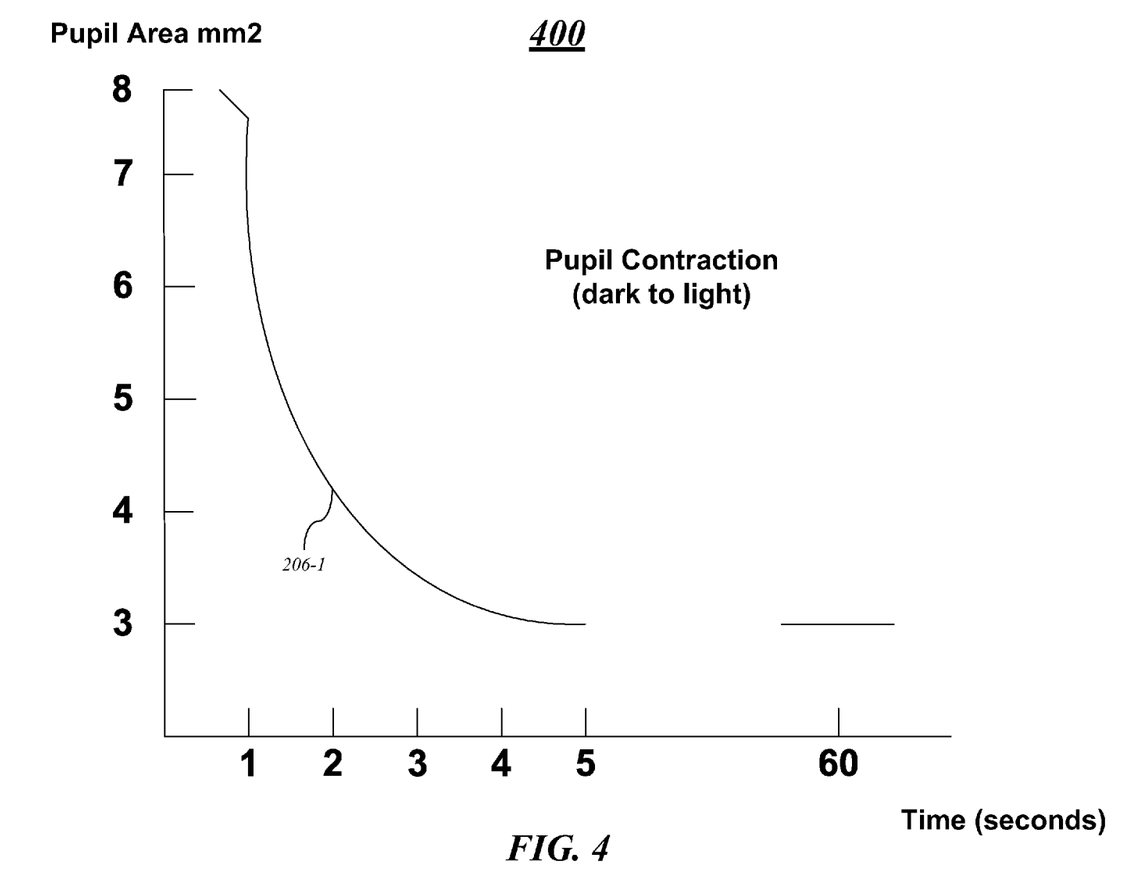
FIG. 4 illustrates an exemplary pupillary light reflex graph.

FIG. 4 illustrates a pupillary light reflex graph 400. The pupillary light reflex graph 400 illustrates an example of a first pupil size response curve 206-1 illustrating a change in pupil size over time in response to changes in ambient light levels from lower luminance to higher luminance. The y-axis represents different pupil sizes (in mm$^2$) from 8 mm to 3 mm. The x-axis represents time in seconds from 0 to 60 seconds. It may be appreciated that different dimensions may be used for the y-axis to accommodate greater variations in pupil size, with corresponding changes to the first pupil size response curve 206-1, as desired for a given implementation. The pupillary light reflex graph 400 is an exemplary graph derived from a document titled "The Reaction of the Eye to Light," Prentice Reeves Research Laboratory, Transactions of Optical Society, October 1920, which is hereby incorporated by reference. The embodiments, however, are not limited to this example.

The first pupil size response curve 206-1 illustrates changes in pupil size over time as caused by the pupillary light reflex when a human eye moves from a darker field of 1 mL to a lighter field of over 100 mL. As shown by the first pupil size response curve 206-1, pupil size contracts faster (from approximately 8 mm to 4 mm) during the first 2 seconds when first exposed to 100 mL of ambient light, and then more slowly (from approximately 4 mm to 3 mm) between 2 seconds and 60 seconds afterwards.

The luminance module 204 may select the first pupil size response curve 206-1 when a target pupil size 304 is smaller than a current pupil size 306 (or vice-versa depending on implementation). Continuing with our previous example as described with reference to FIG. 3, the luminance module 204 compares the current pupil size 306 of 17 mm with the target pupil size 304 of 3 mm, and selects the first pupil size response curve 206-1 based on the comparison results.

Figure 5:
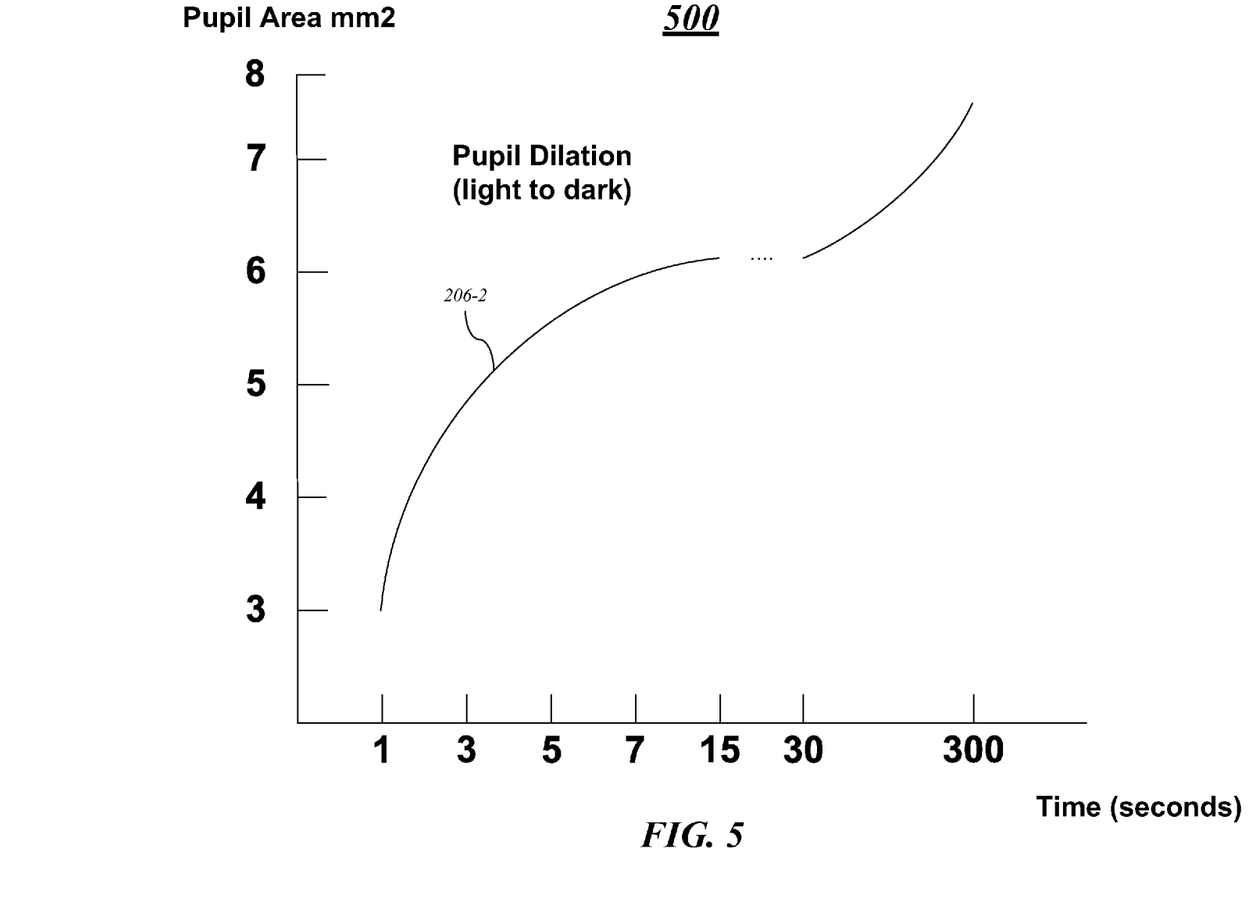
FIG. 5 illustrates an exemplary pupillary light reflex graph.

FIG. 5 illustrates a pupillary light reflex graph 500. The pupillary light reflex graph 500 illustrates an example of a second pupil size response curve 206-2 illustrating a change in pupil size over time in response to changes in ambient light levels from higher luminance to lower luminance. The y-axis represents different pupil sizes (in mm$^2$) from 8 mm to 3 mm. The x-axis represents time in seconds from 0 to 300 seconds. It may be appreciated that different dimensions may be used for the y-axis to accommodate greater variations in pupil size, with corresponding changes to the first pupil size response curve 206-2, as desired for a given implementation. The pupillary light reflex graph 500 is an exemplary graph derived from a document titled "The Reaction of the Eye to Light," Prentice Reeves Research Laboratory, Transactions of Optical Society, October 1920. The embodiments, however, are not limited to this example.

The second pupil size response curve 206-2 illustrates changes in pupil size over time as caused by the pupillary light reflex when a human eye moves from a lighter field of 100 mL to a darker field of 1 mL. As shown by the second pupil size response curve 206-2, pupil size dilates or expands faster (from approximately 3 mm to 6 mm) during the first 15 seconds when first exposed to 1 mL of ambient light, and then more slowly (from approximately 6 mm to 8 mm) between 15 seconds and 300 seconds afterwards.

The luminance module 204 may select the second pupil size response curve 206-2 when the target pupil size 304 is larger than the current pupil size 306. Referring again to the luminance graph 300 described with reference to FIG. 3, assume a target pupil size 308 is approximately 15 mm and a current pupil size 310 is approximately 3 mm since the mobile computing device 100 was in an environment with a higher luminance value of 100 mL prior to moving. The luminance module 204 compares the current pupil size 310 of 3 mm with the target pupil size 308 of 15 mm, and selects the second pupil size response curve 206-2 based on the comparison results.

Once one of the first or second pupil size response curves 206-1, 206-2 have been selected, the luminance module 204 may determine a target pupil size from a selected pupil size response curve 206-1, 206-2. The luminance module 204 may then convert the target pupil size determined from the selected pupil size response curve 206-1, 206-2 to a standard unit of luminance, such as $cd/m^2$ or nitere (nits), and then to one or more display brightness control values. The luminance module 204 may output the display brightness control values to the power management module 170 and/or the display 110 to modify brightness levels for the display 110 of the mobile computing device 100 based on the brightness control values. This process may be continuously repeated at defined time intervals until the target pupil size reaches a steady state (remains relatively unchanged) and brightness levels for the display 110 are within a target range for the ambient light level measurements and pupil size.

Operations for the above-described embodiments may be further described with reference to one or more logic flows. It may be appreciated that the representative logic flows do not necessarily have to be executed in the order presented, or in any particular order, unless otherwise indicated. Moreover, various activities described with respect to the logic flows can be executed in serial or parallel fashion. The logic flows may be implemented using one or more hardware elements and/or software elements of the described embodiments or alternative elements as desired for a given set of design and performance constraints. For example, the logic flows may be implemented as logic (e.g., computer program instructions) for execution by a logic device (e.g., a general-purpose or specific-purpose computer).

Figure 6:
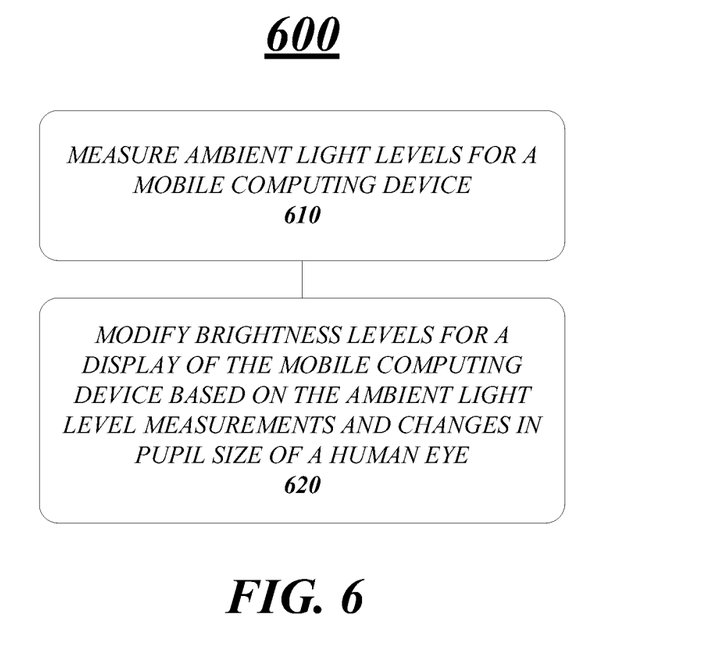
FIG. 6 illustrates one embodiment of a logic flow.

FIG. 6 illustrates one embodiment of a logic flow 600, which may be representative of the operations executed by one or more embodiments described herein. It can be appreciated that the logic flow 600 may comprise various other operations in accordance with the described embodiments.

The logic flow 600 may measure ambient light levels for a mobile computing device at block 610. For example, the ambient light sensor 202 of the display control module 146 may measure ambient light levels for the mobile computing device 100. The ambient light sensor 202 may measure or sample the ambient light levels on a continuous, periodic, aperiodic or on-demand basis. In one embodiment, for example, the ambient light sensor 202 may be arranged to measure ambient light levels at defined time intervals. A length for the defined time interval may vary for any number of reasons, such as an amount of available power remaining for the battery 172, user preference, threshold parameters, and so forth.

The logic flow 600 may modify brightness levels for a display of the mobile computing device based on the ambient light level measurements and changes in pupil size of a human eye at block 620. For example, the luminance module 204 of the display control module 146 may modify brightness levels for the display 110 of the mobile computing device 100 based on the ambient light level measurements and changes in pupil size of a human eye. In one embodiment, the luminance module 204 may utilize at least two pupil size response curves to control a timed ramp between a current brightness level and a target brightness level, such as the pupil size response curves 206-1, 206-2. In this manner, the timed ramp corresponds to contraction or dilation of a human eye, thereby ensuring a more consistent perceived brightness level and more comfortable viewing experience for a user.

Although embodiments have been described as implemented in the mobile computing device 100, it may be appreciated that embodiments may be implemented in any electronic device having a display that emits light and a computing system to control brightness for the display. Examples of electronic devices suitable for use with embodiments may include without limitation a mobile device, a personal digital assistant, a mobile computing device, a smart phone, a cellular telephone, a handset, a one-way pager, a two-way pager, a messaging device, a computer, a personal computer (PC), a desktop computer, a laptop computer, a notebook computer, a handheld computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, television, digital television, set top box, alarm clocks, global positioning system (GPS) devices (handheld and automotive), navigation systems, universal remotes, automotive interior lighting and dashboard illumination, kitchen appliances (e.g., microwave ovens), wireless access point, base station, subscriber station, mobile subscriber center, radio network controller, router, hub, gateway, bridge, switch, machine, or combination thereof. The embodiments are not limited in this context.

In various embodiments, the logic flow 600 may comprise, or be implemented as, executable computer program instructions. The executable computer program instructions may be implemented by software, firmware, a module, an application, a program, a subroutine, instructions, an instruction set, computing code, words, values, symbols or combination thereof. The executable computer program instructions may include any suitable type of code, such as source code, compiled code, interpreted code, executable code, static code, dynamic code, and the like. The executable computer program instructions may be implemented according to a predefined computer language, manner or syntax, for instructing a computer to perform a certain function. The executable computer program instructions may be implemented using any suitable high-level, low-level, object-oriented, visual, compiled and/or interpreted programming language, such as C, C++, Java, BASIC, Perl, Matlab, Pascal, Visual BASIC, assembly language, and others.

In various embodiments, the logic flow 600 may comprise, or be implemented as, executable computer program instructions stored in an article of manufacture and/or computer-readable storage medium. The article and/or computer-readable storage medium may store executable computer program instructions that, when executed by a computer, cause the computer to perform methods and/or operations in accordance with the described embodiments. The article and/or computer-readable storage medium may be implemented by various systems and/or devices in accordance with the described embodiments. In such embodiments, a computer may include any suitable computer platform, device, system, or the like implemented using any suitable combination of hardware and/or software.

The article and/or computer-readable storage medium may comprise one or more types of computer-readable storage media capable of storing data, including volatile memory or, non-volatile memory, removable or non-removable memory, erasable or non-erasable memory, writeable or re-writeable memory, and so forth. Examples of computer-readable storage media may include, without limitation, random-access memory (RAM), dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other suitable type of computer-readable storage media in accordance with the described embodiments.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within registers and/or memories into other data similarly represented as physical quantities within the memories, registers or other such information storage, transmission or display devices.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a computer, a firmware element embedded in hardware, or any combination thereof.

While certain features of the embodiments have been illustrated as described above, many modifications, substitutions, changes and equivalents will now occur to those skilled in the art. It is therefore to be understood that the appended claims are intended to cover all such modifications and changes as fall within the true spirit of the embodiments.

The invention claimed is:

1. A method, comprising:
measuring ambient light levels for a mobile computing device;
determining a target pupil size based on the ambient light level measurements;
comparing a target pupil size with a current pupil size;
selecting a pupil size response curve based on a comparison of a target pupil size and a current pupil size;
determining a target pupil size from a selected pupil size response curve;
converting a target pupil size determined from a selected pupil size response curve to one or more display brightness control values; and
modifying brightness levels for the display of the mobile computing device based on one or more brightness control values and a timed ramp, wherein the time ramp is to provide a transition to a brightness level.

2. The method of claim 1, comprising selecting a first pupil size response curve when a target pupil size is smaller than a current pupil size, the first pupil size response curve representing changes in pupil size over time in response to changes in ambient light levels from lower luminance to higher luminance.

3. The method of claim 1, comprising selecting a second pupil size response curve when a target pupil size is larger than a current pupil size, the second pupil size response curve representing changes in pupil size over time in response to changes in ambient light levels from higher luminance to lower luminance.

4. A non-transitory computer-readable storage medium comprising executable computer program instructions that when executed enable a computing system to:
measure ambient light levels for a mobile computing device;
determine a target pupil size based on the ambient light level measurements;
compare a target pupil size with a current pupil size;
select a pupil size response curve based on a comparison of a target pupil size and a current pupil size;
determine a target pupil size from a selected pupil size response curve;
convert a target pupil size determined from a selected pupil size response curve to one or more display brightness control values; and
modify brightness levels for the display of the mobile computing device based on one or more brightness control values and a timed ramp, wherein the time ramp is to provide a transition to a brightness level.

5. The non-transitory computer-readable storage medium of claim 4, comprising executable computer program instructions that when executed enable the computing system to determine a first target pupil size based on the ambient light level measurements, compare the target pupil size with a current pupil size, select a pupil size response curve based on the comparison, determine a second target pupil size from the selected pupil size response curve, and convert the second target pupil size determined from a selected pupil size response curve to one or more display brightness control values.

6. The non-transitory computer-readable storage medium of claim 4, comprising executable computer program instructions that when executed enable the computing system to select a first pupil size response curve when a target pupil size is smaller than a current pupil size, the first pupil size response curve representing changes in pupil size over time in response to changes in ambient light levels from lower luminance to higher luminance.

7. The non-transitory computer-readable storage medium of claim 4, comprising executable computer program instructions that when executed enable the computing system to select a second pupil size response curve when a target pupil size is larger than a current pupil size, the second pupil size response curve representing changes in pupil size over time in response to changes in ambient light levels from higher luminance to lower luminance.

8. An apparatus, comprising:
a display;
a luminance module operative to:
determine a target pupil size based on the ambient light level measurements;
compare a target pupil size with a current pupil size;
select a pupil size response curve based on a comparison of a target pupil size and a current pupil size;
determine a target pupil size from a selected pupil size response curve;
convert a target pupil size determined from a selected pupil size response curve to one or more display brightness control values; and
a display control module communicatively coupled to the display, the display control module operative to modify brightness levels for the display of the mobile computing device based on one or more brightness control values and a timed ramp, wherein the time ramp is to provide a transition to a brightness level.

9. The apparatus of claim 8, the display control module comprising an ambient light sensor operative to measure ambient light levels within a defined field.

10. The apparatus of claim 8, the display control module comprising the luminance module operative to determine a first target pupil size based on the ambient light level measurements, compare the target pupil size with a current pupil size, select a pupil size response curve based on the comparison, determine a second target pupil size from the selected pupil size response curve, and convert the second target pupil size determined from a selected pupil size response curve to one or more display brightness control values.

11. The apparatus of claim 8, the display control module comprising the luminance module operative to select a first pupil size response curve when a target pupil size is smaller than a current pupil size, the first pupil size response curve representing changes in pupil size over time in response to changes in ambient light levels from lower luminance to higher luminance.

12. The apparatus of claim 8, the display control module comprising the luminance module operative to select a second pupil size response curve when a target pupil size is larger than a current pupil size, the second pupil size response curve representing changes in pupil size over time in response to changes in ambient light levels from higher luminance to lower luminance.

* * * * *

UNITED STATES PATENT AND TRADEMARK OFFICE
CERTIFICATE OF CORRECTION

| | | |
|---|---|---|
| PATENT NO. | : 8,537,174 B2 | |
| APPLICATION NO. | : 12/574540 | |
| DATED | : September 17, 2013 | |
| INVENTOR(S) | : Christopher L Capener | |

It is certified that error appears in the above-identified patent and that said Letters Patent is hereby corrected as shown below:

In the Claims

Column 13, line 54, in Claim 1, delete "time" and insert -- timed --, therefor.

Column 14, line 18, in Claim 4, delete "time" and insert -- timed --, therefor.

Column 14, line 66, in Claim 8, delete "time" and insert -- timed --, therefor.

Signed and Sealed this
Twenty-third Day of September, 2014

Michelle K. Lee
*Deputy Director of the United States Patent and Trademark Office*